United States Patent [19]

Scragg

[11] 4,374,288
[45] Feb. 15, 1983

[54] ELECTROMAGNETIC PROCESS AND APPARATUS FOR MAKING METHANOL

[76] Inventor: Robert L. Scragg, 4210 Prices Creek Rd., Huntington, W. Va. 25701

[21] Appl. No.: 217,501

[22] Filed: Dec. 17, 1980

[51] Int. Cl.³ .................. B01J 19/12; C07C 27/14; C07C 29/48
[52] U.S. Cl. .................................. 568/910; 48/65; 48/197 R; 422/186.04; 422/199; 422/200
[58] Field of Search ............... 422/186, 2 CC, 242, 422/199, 186.04; 568/910, 950; 204/77, 165, 168; 48/65, 197 R; 250/531, 542

[56] References Cited

U.S. PATENT DOCUMENTS

| | | | |
|---|---|---|---|
| 2,462,301 | 2/1949 | Bludworth et al. | |
| 2,801,260 | 7/1957 | Lake | 568/910 |
| 2,824,131 | 2/1958 | Di Nardo et al. | |
| 2,922,809 | 1/1960 | Oberdorfer | |
| 3,067,115 | 12/1962 | Clingman | 568/950 |
| 3,092,667 | 6/1963 | Murphy | 568/910 |
| 3,205,162 | 9/1975 | MacLean | 204/168 |
| 3,445,191 | 5/1969 | Bruning et al. | 422/186 |
| 3,745,193 | 7/1973 | Riegel et al. | 568/910 |
| 3,993,672 | 11/1976 | Arzoumanian et al. | 568/910 X |
| 4,101,394 | 7/1978 | Johnson | |
| 4,214,962 | 7/1980 | Pincon | 422/186 X |
| 4,243,613 | 1/1981 | Brockhaus et al. | 568/910 |

FOREIGN PATENT DOCUMENTS

| | | | |
|---|---|---|---|
| 1302390 | 12/1970 | Fed. Rep. of Germany | 250/542 |
| 1302391 | 5/1971 | Fed. Rep. of Germany | 250/542 |

Primary Examiner—Bradley Garris
Attorney, Agent, or Firm—Cushman, Darby and Cushman

[57] ABSTRACT

An electromagnetic methanol reactor system which includes an enclosed reactor chamber having a pair of electrodes positioned in the chamber and spaced from the walls thereof. An electromagnetic field is generated across the electrodes wherein the field has sufficient strength to atomize oxygen. Methane is continuously supplied to the chamber and oxygen is supplied to the chamber between the electrodes so that the oxygen is atomized. The oxygen combines with the methane to form methanol.

11 Claims, 2 Drawing Figures

ELECTROMAGNETIC PROCESS AND APPARATUS FOR MAKING METHANOL

BACKGROUND OF THE INVENTION

The present invention relates to a system of producing methanol.

The most recent technique for methanol synthesis involves a low pressure process by which synthesis gas is prepared. This synthesis gas is prepared by the steam reforming or partial oxidation of a liquid or gaseous hydrocarbon feedstock or by direct combination of carbon dioxide with purified hydrogen rich gases. Typically, naphtha or natural gas feedstock is desulfurized, preheated, mixed with a superheated steam and then reacted over a conventional catalyst in a multi-tubular reformer. After cooling, the synthesis gas is compressed to the required synthesis pressure. The synthesis gas is passed into a hot-wall convertor over a low pressure methanol synthesis catalyst at a temperature range of 250° to 270° C. The crude methanol thus formed is condensed and separated from the uncondensed gases which are recycled with makeup synthesis gas and fed back to the converter. See, for example, page 733 of the "Chemical and Process Technology Encyclopedia".

In the aforementioned process and in other processes of producing methanol by techniques known today, it is necessary to provide production facilities where a large amount of hydrogen and carbon monoxide are produced by environmentally dangerous processes, by methane cracking and coking. These facilities are environmentally limited to certain heavy industrial areas of the world and necessitate long-range and expensive transport of the finished methanol. The transportation expense offsets the economic production of methanol in the volume heretofore contemplated.

Merthanol, wood alcohol, has been and still is a key chemical used in the production of many industrial and consumer products and is now being sought after as a fuel. Thus, as petroleum products become less available and more expensive, the Government and consumers are seeking ways and techniques for reducing existing fuel shortages and the cost of new fuels. For example, see "Gasohol, A Technical Memorandum", September 1979; Congress of the United States, Office of Technology Assessment (OTA), Washington, D.C. 20510, page 60. In the introduction, this Memorandun states "In fiscal year 1979, OTA estimated that federal expenditures of between $13 and $17 million directly supported the development of alcohol fuels from biomass. In fiscal year 1980 the Administration's research activities are expected to be funded at a level between $18 and $25 million. Additional subsidies include $40 million in loan guarantees, exemption of the federal excise tax on gasohol (for domestic production and imports), eligibility of alcohol fuels for entitlement awards and an investment tax credit of 20% on alcohol fuels facilities." The most promising fuel to alleviate current and anticipated shortages is methanol. Methanol is produced from carbon feedstocks such as natural gas (methane) and coal which are in plentiful supply and are not dependent on grain as is ethanol. Methanol can be mixed with gasoline to form gasohol or even used independently as a fuel. Methanol, as a fuel, has a research octane rating of 106-115 and a motor octane rating of 88-92. When 9 parts gasoline are mixed with 1 part methanol, the research octane rating of the mix is increased from 91.1 to 95.5 octane, and the motor octane rating from 82.5 to 84.5 octane. See, for example, pages 4-45, "Energy Technology Handbook", Douglas M. Considine, McGraw-Hill, Inc.

Methanol is also a competitive way of tranporting natural gas from the wellhead to the consumer. Wellhead gas, which is currently being burned off into the atmosphere in many major oil fields outside the United States, is a potentially cheap fuel when converted to methanol and shipped to the marketplace. Other natural gas producing fields that are not accessible to gas pipelines are compressing the gas to liquid natural gas (LNG) and shipping the compressed gas to gasification plants that have access to gas pipelines. The conversion and shipping of methanol to gasification plants is a simpler, safer and more economical way of transporting natural gas. See pages 2-124, "Energy Technology Handbook", Douglas M. Considine, copyrighted 1977, McGraw-Hill, Inc.

It therefore is an object of this invention to provide a method and apparatus for producing methanol by environmentally acceptable techniques.

It is another object of this invention to provide a method and apparatus for producing efficiently and economically both small and large quantities of methanol.

It is another object of this invention to provide a method and apparatus for producing methanol to be used as a fuel or fuel additive from pipeline or wellhead natural gas.

It is another object of this invention to provide a method and apparatus for producing methanol as a transport medium of natural gas from a wellhead to gasification plant.

SHORT STATEMENT OF THE INVENTION

Accordingly, the present invention relates to a method and apparatus for forming methanol. By the method, methane is conveyed to an electromagnetic combustion and condensing reactor. Oxygen is also conveyed into the reactor where it passes through an electromagnetic field and is atomized prior to convergence and combustion with the methane. The atomized oxygen combines stoichiometrically with the methane in an exothermic reaction to generate methanol gas which is condensed in the reactor to form liquid methanol.

BRIEF DESCRIPTION OF THE DRAWINGS

Other objects, features, and advantages of the present invention will now become more fully apparent from the following detailed description of the preferred embodiment, the appended claims, and the accompanying drawings in which:

DETAILED DESCRIPTION OF THE PREFERRED EMBODIMENT

Figure 1:
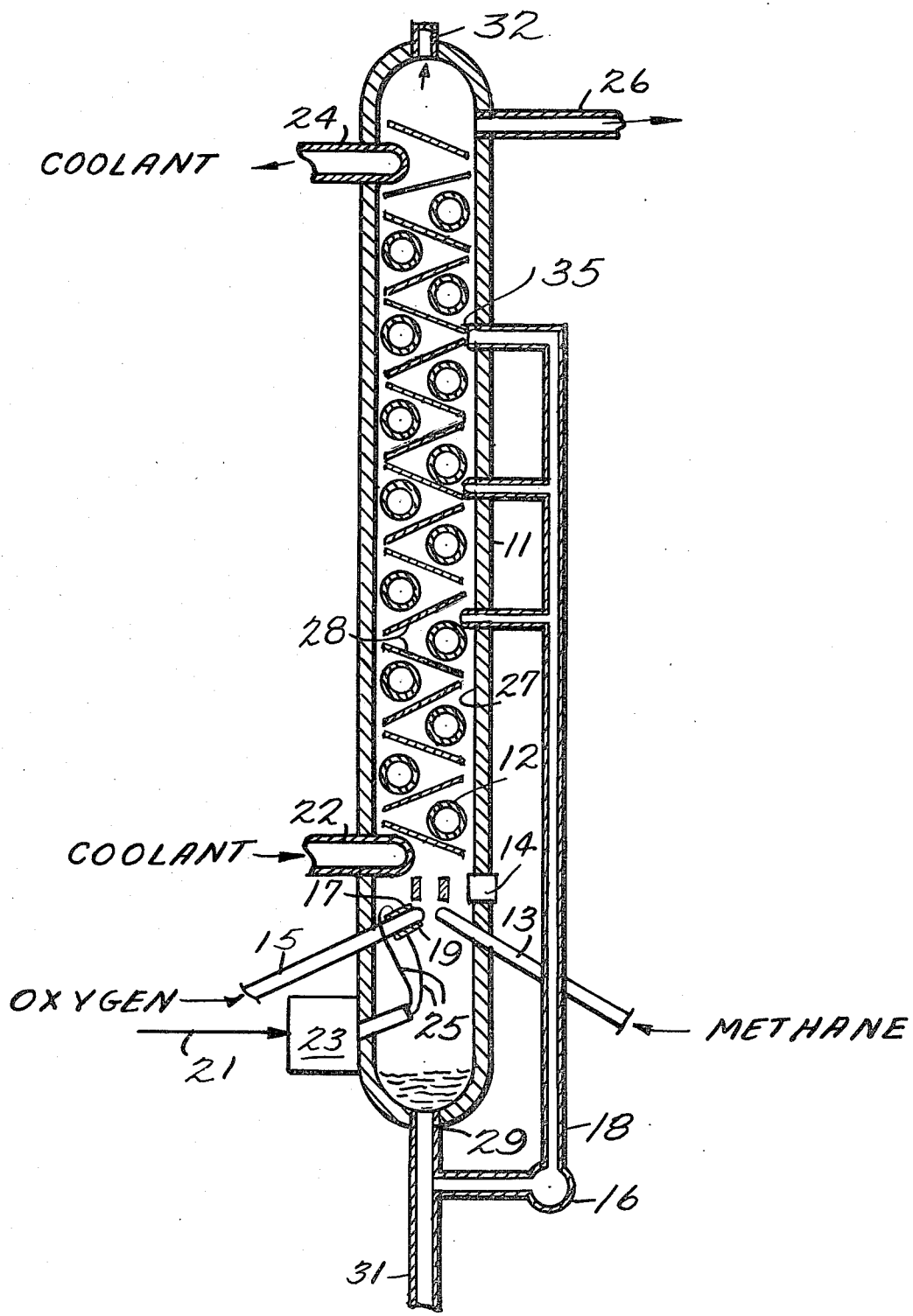
FIG. 1 is a simplified cut-away view of the electromagnetic methanol reactor of the present invention.

As illustrated in FIG. 1, an electromagnetic methanol reactor 11 receives a supply of methane gas from a natural gas supply line 13. The methane is derived from a natural gas supply that has been scrubbed of nitrogen, hydrogen and carbon monoxide trace gases and is typically 96.5% pure methane. Molecular oxygen is fed to the electromagnetic reactor 11 via an oxygen supply line 15. The oxygen is derived from an electrolyzer plant or an air reduction plant and is typically 99.5% pure. The two gases, methane and oxygen, are fed into the reactor 11 at low pressure, under 75 psig, and low velocity. The molecular oxygen is passed between electrostatic plates 17 and 19 which form a gap therebetween. A high voltage transformer 23 is powered by an alternating current supply line 21. The output of transformer 23 is variable and can be adjusted to provide between 1,000 and 10,000 volts on the secondary winding. The spacing of the electrostatic plates 17 and 19 is adjusted to prevent arcing between the plates 17 and 19 depending on the density of the flow volume of the oxygen and the dielectric characteristics of the oxygen. The electrostatic field between the plates 17 and 19 generates heat by hysteresis action sufficient to weaken and break the bond between the oxygen atoms prior to their combination with the methane molecules. The reaction is observed, visibly and spectroscopically, via sight glass 14. The combustion temperature should be in the neighborhood of 1200° C. The oxidation and reduction of the methane molecules by the oxygen atoms forms methyl molecules $CH_3$ and hydroxy molecules OH that combine to form the methanol molecules, i.e., methanol gas, by the following reaction:

$$CH_4 + O \rightarrow CH_3OH$$

The methanol gas thus formed in the reactor chamber 11 rises in the reactor column encountering vortex baffle plates 28 in the center of the reactor column to decrease the velocity of the methanol gas and direct the gas to the walls of the water cooled helical coils 12 and to the air cooled wall 27 of the reactor column. The reactor column wall 27 is air cooled or water cooled to 64° C. or lower which is below the boiling point of methanol liquid. The cooling water passed through the helical coils 12 is conveyed with respect to the coils 12 via lines 22 and 24 and reduces the temperature of the methanol gas inside the reactor 11 below the critical temperature of 240° C. and the critical pressure of 78.7 atmospheres to a temperature of less than 112° C. and to a pressure of less than 5 atmospheres. The methanol gas cools as its velocity is slowed during its rise up the reactor column 11 and as it is repeatedly directed to the walls of the water cooled helical coils 12 and the cool wall 27 of the reactor column 11. The methanol gas is cooled and pressurized to form liquid methanol prior to reaching the top of the reactor 11 column because it condenses on the walls of the water cooled helical coils 12 and the reactor wall 27. To increase the rate of reaction, methanol liquid is taken from line 31 via line 18 and pumped via pump 16 into spray nozzles 35 along the reactor column wall 27. The liquid methanol is atomized by the spray nozzles 35 and vaporized on contact with the hot methanol gas producing methanol vapor. The methanol vapor produced by the reaction condenses rapidly on contact with the cool reactor column wall 27 and helical coils 12. Any methanol gas not condensed prior to reaching the top of the reactor column 11 is vented via line 26 to an additional condensing stage. As the condensed methanol vapors accumulate on the walls of the helical coils 12 and the wall 27 of the reactor column 11, the liquid condensate, i.e., methanol liquid, gravitates down the wall 27 to the bottom of the reactor 11 and down through line 31 via port 29 to a storage reservoir. Port 29 and line 31 are designed to retain liquid methanol to a desired level in the bottom of the reactor 11. Light trace gases, primarily, nitrogen, accumulate in the reactor dome and build up pressure in the reactor which increases the rate of condensation of the methanol gas at the top end of the reactor column 11. The pressure is maintained at or below a predetermined level in the reactor column 11 to prevent back pressure on the burner at the bottom of the reactor 11 thereby sustaining the desired stoichiometric combination of oxygen and methane, and is vented by a pressure loaded check valve 32. The dimensions of the reactor 11 are directly proportional to the desired volume of the reactants, the cooling medium and pressure levels of the reactor.

Figure 2:
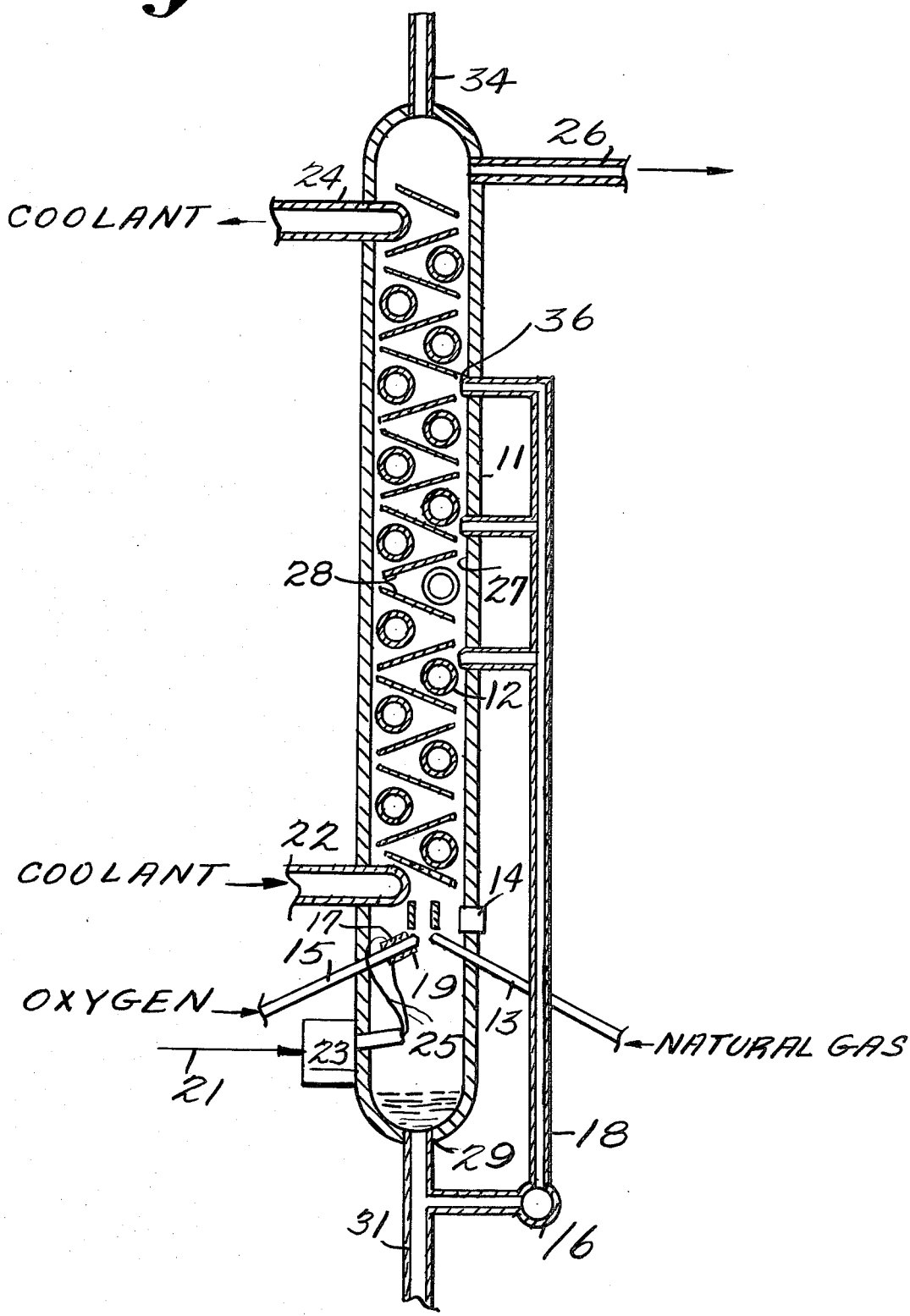
FIG. 2 is a simplified cut-away view of an alternate embodiment of the electromagnetic reactor of the present invention.

Refer now to FIG. 2 where there is illustrated an alternate embodiment of the electromagnetic reactor of the present invention. As illustrated in FIG. 2, an electromagnetic methanol reactor 11 receives a supply of natural gas via supply line 13. The natural gas being typically composed of 96.5% methane, 3% nitrogen, 0.5% hydrogen and a trace of carbon monoxide when furnished from a natural gas supplier or after treatment of wellhead gas. Molecular oxygen is fed to the electromagnetic reactor 11 via supply line 15. The oxygen is derived from an electrolyzer plant, an air reduction plant or from air. The oxygen derived from ambient air is typically 75% nitrogen, 24% oxygen and 1% trace gases, e.g., helium, hydrogen, neon, argon, etc. The gases, natural gas and atmospheric oxygen, are fed into the reactor 11 at low pressure, e.g., under 75 psig, and at a low velocity. The molecular oxygen and/or air is passed between electrostatic plates 17 and 19 which form a gap therebetween. A high voltage transformer 23 is energized from an alternating current supply line 21. The output of transformer 23 is variable between 1,000 and 10,000 volts depending upon the input voltage and, of course, the transformer ratio. The spacing of the electrostatic plates 17 and 19 is adjusted to prevent arcing between the plates 17 and 19 depending on the density of the flow of the atmospheric oxygen and the dielectric characteristics thereof. The electrostatic field between the plates 17 and 19 weakens and breaks the bond between the oxygen atoms prior to their combustion with the methane molecules in the natural gas. Other molecules mixed with the oxygen when it is derived from air, such as nitrogen, are not atomized. The electrostatic plates are adjusted to break oxygen molecular bonds with a heat of atomization of 59.5 Kcal per g-atom. Nitrogen requires 113 Kcal per g-atom. The oxidation of the methane molecules by the oxygen atoms forms methanol molecules, i.e., methanol gas, with a weight of 32 grams per mole. The nitrogen in the reactor 11 does not chemically react and form other molecular bonds due to the low heat of the methaneoxygen burn. The methanol gas which is formed by the process is cooled and condensed by the same method described in connection with FIG. 1. Nitrogen at 28 grams per mole, trace hydrogen at 2 grams per mole, which are not reacted with atomic oxygen, and trace carbon monoxide at 28 grams per mole are vented out of the reactor via port 33 through stack line 34. The size of port 33 and stack line 34 are designed to hold a predetermined back pressure on the chamber to accelerate the rate of condensation of the methanol gas.

While the present invention has been disclosed in connection with the preferred embodiment thereof, other design configurations of gas reacting and condensing columns with other types of cooling systems may be utilized to react methane and atomic oxygen to form methanol gas and to condense said gas to methanol liquid and it should be understood that other embodiments of the invention may be used in accordance with the spirit and scope of the invention as defined by the appended claims.

What is claimed is:

1. A methanol reactor comprising:
   an enclosed reactor chamber;
   a pair of electrodes positioned in said chamber and spaced from the walls thereof;
   means for generating an electric field across said electrodes, said electrodes being spaced with respect to one another to prevent dielectric breakdown therebetween;
   means for continuously supplying methane to said chamber at a low velocity; and
   means for continuously supplying oxygen at a low velocity between said electrodes, said electric field being of sufficient strength to atomize said oxygen, said atomized oxygen combining with said methane to form methanol.

2. A methanol forming system comprising:
   an enclosed reactor chamber;
   a pair of electrodes positioned in said chamber and connected to a source of high voltage, said voltage generating a hysteresis field between said electrodes for generating heat sufficient to atomize oxygen, said electrodes being spaced with respect to one another to prevent dielectric breakdown therebetween;
   means for supplying said oxygen at a low velocity to said reactor chamber and between said electrodes to thereby atomize said oxygen; and
   means for supplying methane at a low velocity to said reactor chamber wherein said atomized oxygen and methane combine to form methanol.

3. The methanol forming system of claim 2 further comprising means for cooling formed methanol gas to below its vaporizing temperature.

4. The methanol forming system of claim 3 wherein said cooling means includes means for conducting a cool fluid through a substantial portion of said reactor chamber.

5. The methanol forming system of claim 4 wherein said cooling means further comprises means for recirculating liquid methanol into said chamber.

6. The methanol forming system of claim 3 further comprising means for maintaining the pressure level in said reactor chamber below a predetermined level.

7. The methanol forming system of claim 2 further comprising means for maintaining the temperature of the oxygen-methane reaction sufficiently low to inhibit the formation of formaldehyde.

8. A method of forming methanol comprising the steps of:
   continuously supplying methane gas at a low velocity to an enclosed reactor chamber;
   generating an electromagnetic field within said reactor chamber, said electromagnetic field being sufficient to atomize oxygen but insufficient to cause arcing through said oxygen; and
   continuously supplying oxygen at a low velocity to said chamber, said oxygen being atomized by said electromagnetic field, said atomized oxygen combining with said methane gas to form methanol.

9. A method of forming methanol comprising the steps of:
   supplying methane gas at a low velocity to an enclosed reactor chamber;
   generating an electromagnetic hysteresis field within said reactor chamber, said electromagnetic field generating sufficient heat to atomize oxygen; and
   supplying oxygen at a low velocity to said chamber, said oxygen being atomized by said field, said atomized oxygen combining with said methane gas to form methanol.

10. The method of claim 9 further comprising the step of maintaining the temperature of the oxygen-methane reaction sufficiently low to inhibit the formation of formaldehyde.

11. The method of claim 9 further comprising the step of converting said methanol to liquid methanol by cooling said methanol to below its vaporizing temperature.

* * * * *